(12) United States Patent
Berendes et al.

(10) Patent No.: US 7,553,970 B2
(45) Date of Patent: Jun. 30, 2009

(54) PROCESS FOR PREPARING 3-HETEROARYL-3-HYDROXYPROPANOIC ACID DERIVATIVES

(75) Inventors: Frank Berendes, Münster (DE); Markus Eckert, Shanghai (CN); Nils Brinkmann, Leverkusen (DE); Claus Dreisbach, Leichlingen (DE); Ruth Meissner, Leverkusen (DE); Rainhard Koch, Köln (DE)

(73) Assignee: Lanxess Deutschland GmbH, Leverkusen (DE)

( * ) Notice: Subject to any disclaimer, the term of this patent is extended or adjusted under 35 U.S.C. 154(b) by 0 days.

(21) Appl. No.: 10/669,424

(22) Filed: Sep. 24, 2003

(65) Prior Publication Data
US 2004/0181058 A1 Sep. 16, 2004

(30) Foreign Application Priority Data
Sep. 26, 2002 (DE) .............................. 102 44 811

(51) Int. Cl.
*C07D 211/70* (2006.01)
*C07D 211/82* (2006.01)
*C07D 213/24* (2006.01)
*C07D 213/00* (2006.01)
*C07D 213/46* (2006.01)
*C07D 333/22* (2006.01)
*C07D 333/16* (2006.01)
*C07D 333/18* (2006.01)
*C07D 333/08* (2006.01)
*C07D 307/02* (2006.01)

(52) U.S. Cl. .................... 546/315; 546/334; 546/339; 546/340; 549/70; 549/78; 549/79; 549/483; 549/497

(58) Field of Classification Search ................ 549/75, 549/74, 76, 77, 78, 79, 70, 483, 497; 435/117, 435/122, 125, 126; 535/117, 122, 125, 126; 546/315, 334, 339, 340
See application file for complete search history.

(56) References Cited

U.S. PATENT DOCUMENTS

| 5,104,899 | A  | 4/1992  | Young et al. ............ 514/646 |
| 6,515,134 | B1 | 2/2003  | Amano et al. ........... 546/315 |
| 6,642,387 | B2 | 11/2003 | Amano et al. ........... 546/314 |
| 2003/0130521 | A1 | 7/2003 | Amano et al. ........... 546/290 |

FOREIGN PATENT DOCUMENTS

| EP | 447 938 | 10/1995 |
| WO | 98 54350 | 12/1998 |
| WO | 03 078418 | 9/2003 |
| WO | WO 2004/024708 | * 3/2004 |

OTHER PUBLICATIONS

Dehli et al., Enantio-and chemoselective bioreduction of of β-keto nitriles by the fungus *Curvularia lunata*, Tetrahedron, vol. 11, pp. 3693-3700.*
Wermuth G Camille,The Practice od Medicinal Chemistry, Harcourt Brace and Company, pp. 204-214.*
CABONab et al. "The Microbial Reduction of 2-chloro-3-oxoesters", Tetrahedron, vol. 6, pp. 2199-2210.*
Fogagnolo M et al: "Homochiral (R)- and (S)-1-heteroaryl- and 1-aryl-2-propanols via microbial redox" Tetrahedron Asymmetry, Elsevier Science Publishers, Amsterdam, NL, Bd. 9, Nr. 13, Jul. 3, 1998, Seiten 2317-2327, XP004131378 ISSN: 0957-4166 Tabelle 2.
Furuichi A et al: "The Use of Microorganisms in Organic Synthesis 5. Microbiological Asymmetric Reduction of Methyl-2-Methyl-3-2-Thienyl-3-Oxo Propionate" Chemical and Pharmaceutical Bulletin (Tokyo), Bd. 32, Nr. 4, 1984, Seiten 1619-1623, XP001179422 ISSN: 0009-2363 Abbildung 1.
Quiros M et al: "Enantioselective reduction of beta-keto amides by the fungus *Mortierella isabellina*" Tetrahedron: Asymmetry, Elsevier Science Publishers, Amsterdam, NL, Bd. 8, Nr. 18, Sep. 25, 1997, Seiten 3035-3038, XP004090508 ISSN: 0957-4166 Zusammenfassung Tabelle 1, Produkt 2a-c.
Sybesma et al., Biocatalysis and Biotransformation (month unavailable) 1998. vol. 16, "Reductions of 3-Oxo Esters by Baker's Yeast: Current Status", pp. 95-134.
Dahl et al., Tetrahedron: Asymmetry 10, (month unavailable) (1999), "Baker's yeast: improving the D-stereoselectivity in reduction of 3-oxo-esters", pp. 551-559.
Dehli et al., Tetrahedron Asymmetry 11 (month unavailable) (2000) "Enantio- and chemoselective bioreduction of β-keto nitriles by the fungus *Curvularia lunata*", pp. 3693-3700.
Hayakawa et al., Tetrahedron Letters 39, (month unavailable) (1998) "Control of Enantio-selectivity in the Bakers' Yeast Reduction of β-Keto Ester Derivatives in the Presence of a Sulfur Compound", pp. 67-70.
Cabon et al., Tetrahedron: Asymmetry vol. 6, No. 9, (month unavailable) 1995, "The Microbial Reduction of 2-Chloro-3-oxoesters" pp. 2199-2210.
Smallridge et al., Tetrahedron Letters vol. 39, (month unavailable) (1998), "Enzymatic Alkylation of α-Cyanoketones by Bakers Yeast", pp. 5121-5124.
Chênevert et al., Tetrahedron vol. 48, No. 33 (month unavailable) 1992, "Asymmetric Synthesis of Both Enantiomers of Fluoxetine via Microbiological Reduction of Ethyl Benzoylacetate", pp. 6769-6776.
Kumar et al., Tetrahedron Letters, vol. 32, No. 16, (month unavailable) 1991, "A New Chemo-enzymatic Enantioselective Synthesis of R-(-)-Tomoxetine, (R)- and (S)-Fluoxetine", pp. 1901-1904.
Kalinin et al., Tetrahedron Letters 39, (month unavailable) (1998), "Directed *ortho* Metalation—Cross Coupling Links. Carbamoyl Rendition of the Baker-Venkataraman Rearrangement. Regio-specific Route to Substituted 4-Hydroxycoumarins", pp. 4995-4998.
D.Döpp u. H. Döpp: Carbonsäure-amide (Monoacyl-amine), Houben Weyl "Methoden der Organischen Chemie [Methods of organic chemistry]", 4th Edition, vol. E5, pp. 940-1010.
Houben Weyl "Methoden der Organischen Chemie", 4th edition, vol. E 16 d, pp .987-1003.

* cited by examiner

Primary Examiner—D. Margaret Seaman
Assistant Examiner—Niloofar Rahmani
(74) *Attorney, Agent, or Firm*—Norris McLaughlin & Marcus PA

(57) ABSTRACT

The invention relates to a process for preparing enantiomer-enriched 3-heteroaryl-3-hydroxypropanoic acid derivatives and 3-heteroaryl-1-aminopropan-3-ols, and to their use.

12 Claims, No Drawings

US 7,553,970 B2

PROCESS FOR PREPARING 3-HETEROARYL-3-HYDROXYPROPANOIC ACID DERIVATIVES

BACKGROUND OF THE INVENTION

1. Field of the Invention

The invention relates to a process for preparing enantiomer-enriched 3-heteroaryl-3-hydroxypropanoic acid derivatives and 3-heteroaryl-1-aminopropan-3-ols, and to their use.

2. Brief Description of the Prior Art

3-Heteroaryl-3-hydroxypropanoic acid derivatives and 3-heteroaryl-1-aminopropan-3-ols have gained industrial significance, in particular, as intermediates for producing medicaments. Illustratively, some 3-heteroaryl-3-hydroxypropanoic acid derivatives and 3-heteroaryl-1-aminopropan-3-ols are used as precursor substances for preparing inhibitors of the uptake of serotonin or noradrenaline. In the case of some of these inhibitors, it has been shown that certain enantiomers are not only inactive, or less active, but are even able to exhibit undesirable side-effects (U.S. Pat. No. 5,104,899).

The art-known processes for preparing these enantiomers and the attendant disadvantages are as follows. A process for preparing enantiomer-enriched (1S)-3-(methylamino)-1-(2-thiophenyl)-1-propanol proceeding from 1-(2-thiophenyl)-3-chloropropan-1-one is described in Chirality 2000, 12, 26-29. Following reduction to the racemic 3-chloro-1-(2-thienyl)-1-propanol, the racemate is resolved enzymically and the (S) enantiomer is subjected to further reaction with NaI and methylamine to give (S)-3-(methylamino)-1-(2-thiophenyl) propan-1-ol. This method suffers from the disadvantage that, in principle, only 50% of the desired enantiomer can be obtained when racemates are resolved enzymically and the total yield is therefore economically unacceptable.

It is known that microorganisms, such as yeasts or fungi, can be used to reduce 3-oxocarboxylic acid derivatives enantioselectively to give the corresponding enantiomer-enriched 3-hydroxycarboxylic acid derivatives (see also Sybesma et al., Biocatalysis and Biotransformation, 1998, Vol. 16, 95-134; Dahl et al., Tetrahedron: Asymmetry 10, 1999, 551-559, Dehli et al., Tetrahedron: Asymmetry 11, 2000, 3693-3700, Hayakawa et al, Tetrahedron Letters, 1998, Vol. 39, 67-70, Cabon et al., Tetrahedron: Asymmetry 6, 1995, 2199-2210 and Smallridge et al., Tetrahedron Letters, 1998, Vol. 39, 5121-5124).

In addition, EP-A 447 938 describes the enantioselective synthesis of 2-halo-3-hydroxy-3-phenylpropanoic esters by using various organisms to reduce the 2-halo-3-oxo-3-phenylpropanoic esters.

Furthermore, Chenevert et al., Tetrahedron 1992, Vol.48, 6769-6776 disclose the asymmetric synthesis of both enantiomers of the antidepressant fluoxetine (N-methyl-3-(4-trifluoromethylphenoxy)-3-phenylpropylamine hydrochloride). An important step in the multi-stage synthesis is that of using microorganisms to effect the enantioselective reduction of the ethyl 3-oxo-3-phenylpropanoate.

An analogous synthesis, for preparing (R)-tomoxetine, which acts as an antidepressant, is described in Kumar A. et al., Tetrahedron Letters, 1991, Vol. 32, 1901-1904. Reportedly, the enantioselective reduction of the ethyl 3-oxo-3-phenylpropanoate to give ethyl 3-hydroxy-3-phenylpropanoate is an important step in this synthesis as well.

However, the enantioselective reduction of heteroaryl ketones has not previously been described.

There was still the need to provide a process which makes it possible to prepare enantiomer-enriched 3-heteroaryl-3-hydroxypropanoic acid derivatives.

SUMMARY OF THE INVENTION

In accordance with the foregoing, a process for preparing stereoisomer-enriched 3heteroaryl-3-hydroxypropanoic acid derivatives has now been found, which process is characterized in that compounds of the formula (I)

$$\text{heteroaryl-CO—CH}_2\text{W} \qquad (I),$$

in which heteroaryl is a monocyclic or bicyclic aromatic radical having a total of from 5 to 10 ring atoms, where none, one or two ring atoms, selected from the group oxygen, sulphur and nitrogen, can be present per cycle and one or two can be present in the entire aromatic radical, and where the monocyclic or bicyclic aromatic radical is optionally substituted, once, twice or three times, by radicals which are selected, in each case independently of each other, from the group hydroxyl, $C_1$-$C_8$-alkyl, cyano, COOH, COOM, where M is an alkali metal ion or a half equivalent of an alkaline earth metal ion, COO—($C_1$-$C_4$-alkyl), O—($C_1$-$C_4$-alkyl), N($C_1$-$C_4$-alkyl)$_2$, NH—($C_1$-$C_4$-alkyl), fluorine, $NO_2$, chlorine, bromine, $C_1$-$C_4$-fluoroalkyl, $CONH_2$ or CONH—($C_1$-$C_4$-alkyl), and W is $C(O)YR^1_n$, where Y is=oxygen and n is=1, or Y is nitrogen and n is=2, or W is CN, and $R^1$ are, in each case independently of each other, hydrogen, $C_1$-$C_8$-alkyl, $C_4$-$C_{10}$-aryl or $C_5$-$C_{11}$-arylalkyl or, when Y is nitrogen, the two radicals $R^1$ are together $C_3$-$C_5$ alkylene, are reacted in the presence of microorganisms and/or cell preparations thereof, and in the presence of water having a pH range of from 3 to 11, based on 25° C., and, in this way, enantiomer-enriched compounds of the formula (II),

$$\text{heteroaryl-CH(OH)—CH}_2\text{W} \qquad (II),$$

in which heteroaryl and W have the abovementioned meaning, are obtained.

Within the context of the invention, all the radical definitions, parameters and specifications which are mentioned in general or which are mentioned in preference, as stated above or below, can be combined amongst themselves, that is between the respective ranges and preference ranges as well, in any arbitrary manner.

Within the meaning of the invention, the term enantiomer-enriched encompasses, in particular, enantiomerically pure compounds or arbitrary mixtures of enantiomers in which one enantiomer is present in a larger proportion than the other enantiomer, preferably in a relative proportion of from 60% to 100 mol %, particularly preferably from 80 to 100 mol % and, very particularly preferably, from 90 to 100 mol %.

DETAILED DESCRIPTION OF THE INVENTION

Within the context of the invention, alkyl is, in each case independently, a straight-chain or cyclic, independently thereof branched or unbranched, alkyl radical which can be further substituted by $C_1$-$C_4$-alkoxy radicals. The same applies to the nonaromatic moiety of an arylalkyl radical.

For example, within the context of the invention, $C_1$-$C_4$-alkyl is methyl, ethyl, 2-ethoxyethyl, n-propyl, isopropyl, n-butyl and tert-butyl, while $C_1$-$C_8$-alkyl is, in addition to this, for example, n-pentyl, cyclohexyl, n-hexyl, n-heptyl, n-octyl or iso-octyl.

Fluoroalkyl is, in each case independently, a straight-chain, cyclic, branched or unbranched alkyl radical which is substituted, once, more than once or completely, by fluorine atoms.

For example, $C_1$-$C_4$-fluoroalkyl is trifluoromethyl, 2,2,2-trifluoroethyl, pentafluoroethyl, nonafluorobutyl and heptafluoroisopropyl.

Within the context of the invention, aryl is, for example and preferably, carbocyclic aromatic radicals or heteroaromatic radicals which contain no, one or two, but at least one in the entire heteroaromatic radical, heteroatom(s) which is/are selected from the group nitrogen, sulphur and oxygen.

In addition, the carbocyclic aromatic radicals or heteroaromatic radicals can be substituted by one or two substituents per cycle, which substituents are selected, in each case independently of each other, for example and preferably, from the group hydroxyl, $C_1$-$C_4$-alkyl, cyano, COOH, COOM, where M is an alkali metal ion or a half equivalent of an alkaline earth metal ion, COO—($C_1$-$C_4$-alkyl), O—($C_1$-$C_4$-alkyl), N($C_1$-$C_4$-alkyl)$_2$, NH—($C_1$-$C_4$-alkyl), fluorine, chlorine, bromine, $C_1$-$C_4$-fluoroalkyl, $CONH_2$ or CONH—($C_1$-$C_4$-alkyl). The same applies to the aryl moiety of an arylalkyl radical.

In the formulae (I) and (II), heteroaryl is preferably a monocyclic aromatic radical having a total of 5 or 6 ring atoms in which one or two ring atoms are selected from the group oxygen, sulphur and nitrogen and where the monocyclic aromatic radical contains no, one or two radical(s) which is/are selected, in each case independently of each other, from the group methyl, ethyl, n-propyl, isopropyl, cyano, COOH, COONa, COOK, COO-methyl, COO-ethyl, COO-tert-butyl, COO-phenyl, methoxy, ethoxy, dimethylamino, diethylamino, methylamino, ethylamino, fluorine, chlorine, $NO_2$, trifluoromethyl, pentafluoroethyl, heptafluoroisopropyl, $CONH_2$ and CONH-methyl.

Heteroaryl is, particularly preferably, 2- or 3-thiophenyl, 2- or 3-furanyl, 2- or 3-pyrrolyl, 3- or 4-pyrazolyl, 1-, 2- or 4-thiazolyl, 1-, 2- or 4-oxazolyl, 2-, 4- or 5-imidazolyl, 2-, 3- or 4-pyridyl, 2- or 3-pyrazinyl, 2-, 4- or 5-pyrimidyl, 3-, 4-, 5- or 6-pyridazinyl, 2- or 3-indolyl, 3-indazolyl, indazolyl, 2- or 3-benzo-furanyl, 2- or 3-benzothiophenyl, 2-, 3- or 4-quinolinyl or isoquinolinyl, where each of the radicals mentioned carries no, one or two, and preferably no, substituents which are in each case selected, independently of each other, from the group methyl, ethyl, n-propyl, isopropyl, cyano, methoxy, ethoxy, fluorine, chlorine, trifluoromethyl, pentafluoroethyl and heptafluoroisopropyl.

Heteroaryl is very particularly preferably 2-thiophenyl.

$R^1$ is preferably CN or $COOR^1$, where $R^1$ is hydrogen or methyl or ethyl.

Preferred compounds of the formula (I) are methyl 3-oxo-3-(2-thiophenyl)-propanoate, ethyl 3-oxo-3-(2-thiophenyl)propanoate, methyl 3-oxo-3-(3-thiophenyl)propanoate, ethyl 3-oxo-3-(3-thiophenyl)propanoate, methyl 3-oxo-3-(2-furanyl)propanoate, ethyl 3-oxo-3-(2-furanyl)propanoate, methyl 3-oxo-3-(3-furanyl)propanoate, ethyl 3-oxo-3-(3-furanyl)propanoate, methyl 3-oxo-3-(2-pyridinyl)propanoate, ethyl 3-oxo-3-(2-pyridinyl) propanoate, methyl 3-oxo-3-(3-pyridinyl)propanoate, ethyl 3-oxo-3-(3-pyridinyl)propanoate, methyl 3-oxo-3-(4-pyridinyl)propanoate, ethyl 3-oxo-3-(4-pyridinyl)propanoate, 3-oxo-3-(2-thiophenyl)propanonitrile, 3-oxo-3-(3-thiophenyl)propanonitrile, 3-oxo-3-(2-furanyl)propanonitrile, 3-oxo-3-(3-furanyl)propanonitrile, 3-oxo-3-(2-pyridinyl)propanonitrile, 3-oxo-3-(3-pyridinyl)propanonitrile, 3-oxo-3-(4-pyridinyl)propanonitrile and N-(methyl)-3-oxo-3-(2-thiophenyl)propanamide.

The microorganisms which are preferably employed are bacteria, yeasts or fungi, with both wild types and transformed strains being included.

Microorganisms which are particularly preferred are yeasts and fungi, very particularly preferably those of the genera *Saccharomyces, Geotrichum, Candida, Pichia, Hansenula, Yarrowia, Rhizopus, Mortierella, Mucor, Sporotrichum, Rhodotorula, Trichoderma, Aspergillus, Penicillium, Pullaria, Cunninghamella* and *Curvularia*.

Microorganisms which are even more preferred are *Saccharomyces cereviseae* and *Geotrichum candidum*.

Cell preparations are to be understood as meaning: purified or unpurified lysed cells which can be used either in the moist state or in the dried state, for example as lyophilisates.

Preference is given to using microorganisms.

In a preferred embodiment, the microorganisms are grown, prior to the compounds of the formula (I) being reacted, on complex or mineral nutrient media, using culturing methods which are customary per se for growing the given microorganisms, such as culturing in shaken flasks, batch fermentations, fed-batch fermentations or continuous fermentations, up to an optical density of from 1 to 800, preferably of from 5 to 300, measured at a wavelength of 600 nm ($OD_{600}$), and concentrated, where appropriate, after having been grown.

The microorganisms can be grown, for example, at temperatures of between 10 and 60° C., preferably of between 20 and 40° C.

The pH, when growing the microorganisms can, for example, be between pH 3 and pH 9, preferably between pH 4 and pH 8, particularly preferably between pH 5 and pH 7.5. In this connection, pH values are in each case based on 25° C., within the entire scope of the invention.

The microorganisms can be grown under aerobic or anaerobic conditions; they are preferably grown aerobically.

For the reaction, the compound of the formula (I) is, in a preferred embodiment, added to the microorganisms which are either present in the growth medium or resuspended, where appropriate after prior sedimentation, in an isotonic solution. In this connection, the isotonic solution can be a mineral salt solution or also a nutrient medium for microorganisms.

The mixture can, for example and preferably, be shaken or stirred and, where appropriate, aerated.

The process according to the invention can be carried out in a pH range of from pH 3 to pH 11, preferably of from pH 4 to pH 10, and particularly preferably of from pH 6 to pH 8.

The process according to the invention is, furthermore, customarily carried out at a temperature of from 10 to 60° C., preferably of from 18 to 45° C.

The duration of the reaction can be from 10 min to 96 hours, preferably from 60 min to 72 hours and particularly preferably from 2 to 48 hours.

The process according to the invention can be carried out such that the compounds of the formula (I) are added once, several times or continuously.

The sum of the concentrations of the compounds of the formulae (I) and (II) in the cell suspension can be between 1 and 900 mM, preferably between 2 and 500 mM, particularly preferably between 3 and 250 mM.

In order to increase the solubility of the starting compound in the reaction medium, it is possible, in a preferred embodiment, to add auxiliary substances such as polar, water-miscible solvents, such as glycerol, dimethylformamide or dimethyl sulphoxide, or other auxiliary substances, such as cyclodextrins.

Also, the process according to the invention can be carried out in the presence of an organic solvent, for example in a multiphase system such as, in particular, a two-phase system.

Organic solvents which are suitable for this purpose are, for example, organic solvents which are not miscible with water or which are miscible with at most 10% by volume, such as aliphatic or aromatic, where appropriate chlorinated, solvents, such as petroleum ether, hexane, octane, heptane, toluene, the isomeric xylenes, chlorobenzene, dichloromethane and silicone oils. Frequently, the starting compound can also itself be used as the organic phase.

The compounds of the formula (II) can be isolated in a manner known per se, for example by extracting with an organic solvent, or isolated, if a multiphase system was used, by means of separating off the organic phase and, where appropriate, further extraction and subsequent removal of the organic solvent.

Preference is given to using, for this purpose, solvents such as toluene, ethyl acetate, dichloromethane, isobutyl ketone, cyclohexane and methylcyclohexane, preferably ethyl acetate. The extraction can in this case be effected by either continuously or discontinuously supplying the extracting agent. In the simplest case, the purification is effected by extracting, while shaking, with the previously mentioned extracting agents.

If desired, a further purification can be effected by means of distillation or, in the case of compounds of the formula (I) which are solid at room temperature, by means of recrystallization.

If the process according to the invention is carried out in a multiphase system, the product can also be isolated directly by subjecting the organic phase to fractional distillation.

In a manner according to the invention, the enantiomer-enriched compounds of the formula (II) are obtained, with the stereogenic carbon atom which carries the heteroaryl group and the hydroxyl group usually exhibiting the (S) configuration.

The process according to the invention is particularly suitable for preparing methyl (S)-3-hydroxy-3-(2-thiophenyl)propanoate, ethyl (S)-3-hydroxy-3-(2-thiophenyl)propanoate, methyl (S)-3-hydroxy-3-(3-thiophenyl)propanoate, ethyl (S)-3-hydroxy-3-(3-thiophenyl)propanoate, methyl (S)-3-hydroxy-3-(2-furanyl)propanoate, ethyl (S)-3-hydroxy-3-(2-furanyl)propanoate, methyl (S)-3-hydroxy-3-(3-furanyl)propanoate, ethyl (S)-3-hydroxy-3-(3-furanyl)propanoate, methyl (S)-3-hydroxy-3-(2-pyridinyl)propanoate, ethyl (S)-3-hydroxy-3-(2-pyridinyl)propanoate, methyl (S)-3-hydroxy-3-(3-pyridinyl)propanoate, ethyl (S)-3-hydroxy-3-(3-pyridinyl)propanoate, methyl (S)-3-hydroxy-3-(4-pyridinyl)propanoate, ethyl (S)-3-hydroxy-3-(4-pyridin-yl)propanoate, (S)-3-hydroxy-3-(2-thiophenyl)propanonitrile, (S)-3-hydroxy-3-(3-thiophenyl)propanonitrile, (S)-3-hydroxy-3-(2-furanyl)propanonitrile, (S)-3-hydroxy-3-(3-furanyl)propanonitrile, (S)-3-hydroxy-3-(2-pyridinyl)propanonitrile, (S)-3-hydroxy-3-(3-pyridinyl)propanonitrile, (S)-3-hydroxy-3-(4-pyridinyl)propanonitrile and N-(methyl)-(S)-3-hydroxy-3-(2-thiophenyl)propanamide.

The process according to the invention is furthermore suitable, in particular, as step a) in a process for preparing enantiomer-enriched compounds of the formula (VI),

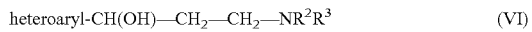

heteroaryl-CH(OH)—CH$_2$—CH$_2$—NR$^2$R$^3$ (VI)

in which heteroaryl has the same meaning as that given under formula (I), and

R$^2$ and R$^3$ are, in each case independently of each other, hydrogen, C$_1$-C$_8$-alkyl, C$_4$-C$_{14}$-aryl or C$_5$-C$_{15}$-arylalkyl, or the two radicals R$^2$ and R$^3$ are together C$_3$-C$_{12}$-alkylene, which is characterized in that in a step a), compounds of the formula (I) are converted, as previously described, into enantiomer-enriched compounds of formula (II)

heteroaryl-CH(OH)—CH$_2$W (II)

where, in each case, heteroaryl and W have the meanings mentioned under formula (I), and in a step b)

i) when W is COOR$^1$ and R$^1$ is hydrogen, C$_1$-C$_8$-alkyl, C$_4$-C$_{10}$-aryl or C$_5$-C$_{11}$-arylalkyl, the enantiomer-enriched compounds of formula (II) are reacted with amines of the formula (III)

HNR$^2$R$^3$ (III)

in which R$^2$ and R$^3$ have the meaning mentioned under formula (VI), to give enantiomer-enriched compounds of the formula (IV), heteroaryl-CH(OH)—CH$_2$—CO—NR$^2$R$^3$ (IV)

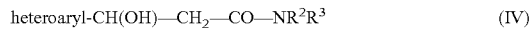

in which heteroaryl, R$^2$ and R$^3$ have the previously mentioned meanings, or ii) when W is CON(R$^1$)$_2$ and the R$^1$ radicals are in each case, independently of each other, hydrogen, C$_1$-C$_8$-alkyl, C$_4$-C$_{10}$-aryl or C$_5$-C$_{11}$-arylalkyl, or the two R$^1$ radicals are together C$_3$-C$_5$-alkylene, the enantiomer-enriched compounds of the formula (II) are converted, where appropriate by reacting with amines of the formula (III), into enantiomer-enriched compounds of the formula (IV), and iii) when W is CN, the compounds of the formula (II) are converted directly, by means of aminolysis/hydrolysis, into compounds of the formula (IV), or are initially converted, by means of hydrolysis, partial hydrolysis or mixed alcoholysis/hydrolysis, into compounds of the formula (V)

heteroaryl-CH(OH)—CH$_2$—CO—R$^4$ (V)

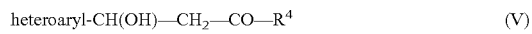

in which heteroaryl has the meaning given under formula (I)

and R$^4$ is OR$^1$ or NH$_2$, where R$^1$ has the abovementioned meaning, and are then converted, by amidation in analogy with i) or, where appropriate, in analogy with ii), into enantiomer-enriched compounds of the formula (IV), and in a step c), the enantiomer-enriched compounds of the formula (IV) are converted, by means of reduction, into enantiomer-enriched compounds of the formula (IV) having the abovementioned meaning.

In the formulae (III), (IV) and (VI), R$^2$ and R$^3$ are particularly preferably, in each case independently, hydrogen, methyl, ethyl, isopropyl, phenyl or benzyl.

In the formulae (III), (IV) and (VI), NR$^1$R$^2$ is, in its entirety, particularly preferably methylamino, ethylamino and isopropylamino.

In the formulae (III), (IV) and (VI), NR$^1$R$^2$ is, in its entirety, very particularly preferably methylamino.

The compounds of the formula (I) which can be used for the process according to the invention comprising steps a), b) and c) are either known from the literature or can be prepared in analogy with the literature.

Compounds of the formula (I) in which W is not CN are preferably obtained by reacting compounds of formula (VII)

heteroaryl-CO—CH$_3$ (VII)

in which heteroaryl has the meaning and preference ranges mentioned under formula (I), with compounds of the formula (VIII),

R$^1$—O—W (VIII)

in which

R$^1$ and W have the same meanings as those which were given under the formula (I), with W not being CN, in the presence of a base.

The reaction of 2-acetylithiophene with dimethyl carbonate, diethyl carbonate, diphenyl carbonate or dibenzyl carbonate, methyl N-methyl carbamate, ethyl N-methyl carbamate, methyl N,N-dimethyl carbamate or ethyl N,N-dimethyl carbamate may be mentioned by way of example.

Such a reaction is described, for example, in Tetrahedron Lett. 1998, 39, 4995 and can be applied in an analogous manner, for example, for the reaction of 2-acetylthiophene with methyl N-methyl carbamate or ethyl N-methyl carbamate to give N-(methyl)-3-oxo-3-(2-thiophenyl)propanamide. It is furthermore also possible to obtain compounds of the formula (Ia)

heteroaryl-CH(OH)—CH$_2$—CO—NHR$^2$ (Ia)

by reacting compounds of the formula (VII) with compounds of the formula (IX)

R$^2$—NCO (IX)

in the presence of a base.

In step b) of the process according to the invention, the enantiomer-enriched compounds of the formula (II) are converted in a manner known per se, in accordance with i), ii) or iii), into enantiomer-enriched compounds of the formula (IV).

Illustratively, Houben Weyl "Methoden der Organischen Chemie [Methods of organic chemistry]", 4th edition, volume E 5, 941-1010 provides a review of the preparation of carboxamides from carboxylic acids, carboxylic esters or other carboxamides.

If liquid or gaseous amines of the formula (III) are employed at room temperature, preference is then given to using solutions of the amines. For example, in the case of methylamine, it is possible to advantageously use solutions consisting of methylamine in water, methanol or ethanol for reacting compounds of the formula (II) in which W is COOR$^1$. Reactions of amines of the formula (III) in the presence of coupling reagents such as 2-halopyridinium or 2-halo-1,3-thiazolium salts, or in the presence of acid cation exchangers, are suitable, for example, for converting free carboxylic acids of the formula (II) into the amides of the formula (IV).

According to step b), enantiomer-enriched compounds of the formula (IV) are then obtained from enantiomer-enriched compounds of the formula (II).

The compounds of the formula (IV) can then be reduced to give the compounds of the formula (VI). The reduction of carboxamides to give the corresponding amines is known in principle and is presented in summary in Houben Weyl "Methoden der Organischen Chemie", 4th edition, volume E 16 d, 987-1003.

Preference is given to reacting compounds of the formula (VI) with complex boron hydrides or aluminium hydrides, such as lithium aluminium hydride, Red-Al® (sodium bis(2-methoxyethoxy)dihydroaluminate) or sodium borohydride.

Particular preference is given to reacting compounds of the formula (VI) with lithium aluminium hydride.

The reductions are preferably carried out at temperatures in the range from room temperature to 150° C., particularly preferably in the range from 50 to 110° C. While the reductions are usually carried out in ethers as solvents, preferably in cyclic ethers such as tetrahydrofuran or dioxane, reactions using Red-Al® can also be carried out in toluene as the solvent.

The enantiomer-enriched compounds of the formula (VI) are obtained in a manner according to the invention.

The following may be mentioned as being preferred compounds of the formula (VI):

(1S)-3-(methylamino)-1-(2-thiophenyl)-1-propanol, (1R)-3-(methylamino)-1-(2-thiophenyl)-1-propanol, (1S)-3-(dimethylamino)-1-(2-thiophenyl)-1-propanol and (1R)-3-(dimethylamino)-1-(2-thiophenyl)-1-propanol, with (1S)-3-(methylamino)-1-(2-thiophenyl)-1-propanol being even more preferred.

The enantiomer-enriched compounds of the formula (VI) which can be prepared in accordance with the invention are particularly suitable for preparing enantiomer-enriched compounds of the formula (X)

heteroaryl-CH(OR$^6$)—CH$_2$—CH$_2$NR$^2$R$^3$ (X)

in which heteroaryl, R$^2$ and R$^3$ have the meanings and preference regions given under formula (I), and R$^6$ is phenyl or naphthyl which can be substituted, not at all, once or more than once, by substituents which are selected, in each case independently of each other, from the group cyano, CO—(C$_1$-C$_{12}$-alkyl), O—(C$_1$-C$_{12}$-alkyl), (C$_1$-C$_{12}$-alkyl), fluorine, chlorine, bromine or C$_1$-C$_{12}$-fluoroalkyl.

R$^6$ is preferably naphthyl.

Preferred compounds of the formula (X) are (S)-N-methyl-3-(1-naphthalenyloxy)-3-(2-thienyl)propylamine and (R)-N-methyl-3-(1-naphthalenyloxy)-3-(2-thienyl)propylamine and their ammonium salts.

The invention therefore also further comprises a process which as step d), encompasses the reaction of enantiomer-enriched compounds of the formula (VI) with compounds of the formula (XI) to give enantiomer-enriched compounds of the formula (X) in the presence of a base.

In formula (XI),

R$^6$-Hal (XI)

R$^6$ has the meaning mentioned under the formula (X), and

Hal is fluorine, chlorine, bromine or iodine, preferably fluorine.

1-Fluoronaphthalene and 4-chlorobenzotrifluoride are preferably used as compounds of the formula (XI).

The bases which can be used are those which are able to at least partially deprotonate the compounds of the formula (VI) at the alcohol function.

These bases include, for example, alkaline earth metal or alkali metal hydrides, hydroxides, amides, alcoholates or carbonates, such as sodium hydride, sodium amide, lithium diethylamide, sodium methoxide, sodium ethoxide, potassium tert-butoxide, sodium hydroxide and potassium hydroxide.

The compounds which can be prepared in accordance with the invention are particularly suitable for use as active compounds in medicaments such as, in particular, inhibitors of serotonin or noradrenaline uptake, or as intermediates thereof.

The process according to the invention enjoys the advantage that it is possible to use readily available starting compounds to synthesize enantiomer-enriched 3-heteroaryl-3-hydroxypropanoic acid derivatives and 3-heteroaryl-1-aminopropan-3-ols, and their secondary products, on an industrial scale in high overall yields, high enantiomer excesses and high purities.

The invention is further described by the following illustrative but non-limiting examples.

EXAMPLES

Examples 1 and 2

Reduction of methyl 3-oxo-(2-thiophenyl)propanoate using Different Strains of the Baker's Yeast *Saccharomyces cereviseae*

The yeast strains (*Saccharomyces cereviseae* NG 247, Uniferm GmbH & Co KG, Monheim; *Saccharomyces cereviseae* Y278, Deutsche Hefe Werke [German Yeast Works] GmbH & Co oHG, Hamburg) were grown overnight, at 28° C. and with shaking (200 rpm), in 100 ml Erlenmeyer flasks containing 25 ml of YM medium (yeast extract, 3.0 g/l; malt extract, 3.0 g/l; peptone, 5.0 g/l; glucose, 10.0 g/l).

Each of the two yeast strains was incubated, at 28° C. and while shaking (200 rpm), in three 1-liter Erlenmeyer flasks which contained 200 ml of YM medium which had previously been inoculated with 12 ml of preliminary culture. Growth was monitored by measuring the optical density at 600 nm ($OD_{600}$). After 6-7 h, the cultures reached an $OD_{600}$ of 3 and were harvested by centrifugation (15 min, 8 000 □g) and stored overnight at 4° C. in a refrigerator. For the reaction, 250 µl of 1 M potassium phosphate buffer (pH 7) and 250 µl of 1 M methyl 3-oxo-(2-thiophenyl)propanoate were added to 5 ml of the cell pellet and the whole was shaken in screw cap 13 ml glass tubes. 300 µl of the reaction mixture were removed at regular intervals and extracted with 300 µl of ethyl acetate or toluene. After the subsequent centrifugation (5 min, 5000 □g) for separating the phases, the organic phase was analysed by chiral gas chromatography. The results are recorded in Tab. 1.

Examples 4 and 5

Reduction of methyl 3-(2-thiophenyl)-3-oxopropanoate using *Geotrichum candidum*

200 ml of YM medium were inoculated, in a 1-liter Erlenmeyer flask and as the 1st preliminary culture, with the strain *Geotrichum candidum* ATCC34614 and the flasks were incubated at 28° C. for 18 h while being shaken. As the 2nd preliminary culture, two 1-liter Erlenmeyer flasks, in each case containing 200 ml of GC medium ($KH_2PO_4$, 11.18 g/l; $K_2HPO_4$, 3.12 g/l; glycerol, 30.0 g/l; yeast extract, 10.0 g/l; polypeptone, 5.0 g/l), were in each case inoculated with 10 ml of the 1st preliminary culture and likewise shaken at 28° C. for 18 h.

As the main culture, a 10 liter fermenter was loaded with 4.6 liters of GC medium and inoculated with 400 ml of the 2nd preliminary culture. The culture was grown at 28° C.

TABLE 1

Reduction of methyl 3-oxo-(2-thiophenyl)propanoate using different yeast strains.

| Example | Yeast strain | [c] of starting compound | Reaction time [h] | Product | Yield | ee (S) |
|---|---|---|---|---|---|---|
| 1 | NG 247 | 50 mM | 24 | OH O structure with thiophene | 75% | >97% |
| 2 | Y278 | 50 mM | 24 | OH O structure with thiophene | 77% | >97% |

Example 3

Reduction of 3-(2-thiophenyl)-3-oxopropano-1-nitrile using *Saccharomyces cereviseae* Y278

The yeast cells were grown, and the reaction was carried out, as described in Examples 1 and 2. The result is recorded in Table 2.

using an aeration rate of 10 l/min and a stirring rate of 800 rpm. After 10 h, the fermenter was harvested. The cells were sedimented by being centrifuged for 15 min at 6000 □g and were then taken up in 100 mM potassium phosphate buffer (PP buffer), pH 6.4, and stored at 4° C. in a refrigerator.

1.8 g of glucose, 9 ml of 1M PP buffer (pH 7.3) and 71 µl (final concentration 20 mM) or 143 µl (final concentration 40 mM) of methyl 3-(2-thiophenyl)-3-oxopropanoate were added to 16 g of moist biomass and the whole was stirred at

TABLE 2

| Example | Yeast strain | Starting compound conc. | Reaction time [h] | Product | Yield of product | ee (S) |
|---|---|---|---|---|---|---|
| 3 | Y278 | 20 mM | 9 | OH structure with thiophene and nitrile | 22% | 85% |

28° C. in a 25 ml Schott bottle using a magnetic stirrer. 300 µl of the reaction mixture were removed at regular intervals and extracted with 300 µl of ethyl acetate or toluene and the organic phase was analysed by gas chromatography. The results were recorded in Table 3.

TABLE 3

Reduction of methyl 3-(2-thiophenyl)-3-oxo-propanoate with the strain Geotrichum candidum ATCC34614.

| Example | Starting compound conc. | Reaction time [h] | Product | Yield of product | ee (S) |
|---|---|---|---|---|---|
| 4 | 20 mM | 10 | methyl 3-hydroxy-3-(2-thiophenyl)propanoate | 71% | >98% |
| 5 | 40 mM | 10 | methyl 3-hydroxy-3-(2-thiophenyl)propanoate | 72% | >98% |

Examples 6 to 12

Reduction of Various β-ketoesters using *Saccharomyces cereviseae*

A preliminary culture of the strain *Saccharomyces cereviseae* NG247 was grown overnight, at 28° C. and while shaking, in 100 ml of YM medium in a 1-liter Erlenmeyer flask. As the main culture, three 1-liter Erlenmeyer flasks, which had each been loaded with 200 ml of YM medium, were in each case inoculated with 10 ml of the preliminary culture and shaken at 28° C. After 6 h, the cultures had reached an optical density of between 7 and 8 as measured at 600 nm ($OD_{600}$). The cells were harvested by centrifugation (15 min, 6000 ×g) and resuspended in 100 mM PP buffer (pH 7)+3% (w/v) glucose as a 10-fold concentrated cell suspension. 1M ethanolic solutions of the test substances were prepared. In the reaction mixtures, the cell suspension was in each case made to 20 mM with respect to the test substance and incubated at 30° C. while being shaken. 300 µl of the reaction mixture were withdrawn at regular intervals and extracted with 300 µl of ethyl acetate or toluene and the organic phase was analysed by gas chromatography. The results are recorded in Tab. 4.

TABLE 4

Enantioselective reduction of heterocyclic β-ketoesters.

| Example | Starting compound | Starting compound conc. | Reaction time [h] | Product | Conversion | ee |
|---|---|---|---|---|---|---|
| 6 | methyl 3-(3-thiophenyl)-3-oxo-propanoate | 20 mM | 24 h | methyl 3-hydroxy-3-(3-thiophenyl)propanoate | 92% | 98% |
| 7 | ethyl 3-(3-furyl)-3-oxo-propanoate | 20 mM | 24 h | ethyl 3-hydroxy-3-(3-furyl)propanoate | 50% | 87% |
| 8 | ethyl 3-(2-furyl)-3-oxo-propanoate | 20 mM | 24 h | ethyl 3-hydroxy-3-(2-furyl)propanoate | 59% | 93% |

TABLE 4-continued

Enantioselective reduction of heterocyclic β-ketoesters.

| Example | Starting compound | Starting compound conc. | Reaction time [h] | Product | Conversion | ee |
|---|---|---|---|---|---|---|
| 9 | (pyridin-4-yl ethyl β-ketoester) | 20 mM | 24 h | (pyridin-4-yl ethyl β-hydroxyester) | 92% | 81% |
| 10 | (pyridin-4-yl methyl β-ketoester) | 20 mM | 24 h | (pyridin-4-yl methyl β-hydroxyester) | 69% | 96% |
| 11 | (pyridin-3-yl methyl β-ketoester) | 20 mM | 24 h | (pyridin-3-yl methyl β-hydroxyester) | 76% | 96% |
| 12 | (pyridin-2-yl ethyl β-ketoester) | 20 mM | 24 h | (pyridin-2-yl ethyl β-hydroxyester) | 99% | 99% |

Example 13

Preparation of methyl 3-oxo-(2-thiophenyl)propanoate 510 ml of dimethyl carbonate and 1 500 ml of toluene were heated to 100° C. in a 2 L flask and a solution of 257 g of 2-acetylthiophene in 510 ml of dimethyl carbonate was then added dropwise within the space of 4 hours. The methanol which was formed in the reaction was distilled off as an azeotrope. 120 ml of conc. sulphuric acid were introduced, in 900 g of ice, into a 4 L flask and the cooled reaction mixture was added such that 40° C. was not exceeded. The mixture was then stirred and the pH was adjusted to pH 1. The phases were separated and the organic phase was extracted three times by shaking with an aqueous solution of sodium sulphate and then concentrated in vacuo. Vacuum distillation of the crude product yielded 278 g of methyl 3-oxo-(2-thiophenyl) propanoate as a transparent, slightly yellowish liquid (98% pure according to GC, 74% of theory).

Example 14

Preparation of N-methyl-(3S)-3-hydroxy-3-(2-thienyl)propanamide 23 g of methyl (3S)-3-hydroxy-3-(2-thienyl)propanoate from experiments described in the Examples 1 and [lacuna] were initially introduced, and 130 ml of a 2-molar methanolic solution of methylamine were added. This mixture is stirred at 60° C. for 4 h, cooled and then concentrated in vacuo. 24 g (purity 87%; 90% of theory) are obtained in this way. The crude product can be used as such for the next step or else recrystallized from methylene chloride and hexane. This yielded 18 g of N-methyl-(3S)-3-hydroxy-3-(2-thienyl)propanamide (75% of theory) in the form of white crystals.

Example 15

Preparation of (1S)-3-(methylamino)-1-(2-thienyl)-1-propanol 350 ml of dry tetrahydrofuran are initially introduced together with 10 g of lithium aluminium hydride and heated to reflux. At the same time, a start is made in adding 17 g of N-methyl-(3S)-3-hydroxy-3-(2-thienyl)propanamide from Example 14, dissolved in 150 g of tetrahydrofuran, dropwise. After this dropwise addition is complete, the mixture is subsequently stirred overnight under reflux. The mixture is then cooled down to room temperature and 200 ml of water are carefully added dropwise. 135 ml of a 10% solution of sodium hydroxide were then added dropwise and the solution was filtered. The solvent was removed in vacuo. 370 ml of 1 N sodium hydroxide solution were added to the crude solution and the whole was extracted 3 times with in each case 370 ml of toluene. The organic phases are combined and the volatile constituents are removed in vacuo, thereby providing 76 g (84% purity, 70% of theory).

Example 16

Purification of (1S)-3-(methylamino)-1-(2-thienyl)-1-propanol 15 g from Example 15 were dissolved in 150 ml of water at boiling heat, after which 5 g of active charcoal were added and the mixture was subsequently stirred under reflux for a further hour. The suspension was filtered in the hot. The filtrate was extracted three times with in each case 100 ml of dichloromethane. The combined organic phases were evaporated and the residue was dissolved, at boiling heat, in 50 ml of cyclohexane; it was then crystallized, during cooling, using 600 ml of petroleum ether. The crystals were filtered, washed with a little petroleum ether and dried. This resulted in 12 g of (1S)-3-(methylamino)-1-(2-thienyl)-1-propanol (98% purity, 93% yield).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing enantiomer-enriched compounds of the formula (VI), heteroaryl-CH(OH)—CH$_2$—CH$_2$—NR$^2$R$^3$ (VI)

in which heteroaryl is a monocyclic aromatic radical having a total of 6 ring atoms, where one or two ring atoms, selected from the group oxygen, sulphur and nitrogen, is present and where the monocyclic aromatic radical is optionally substituted, once, twice or three times, by radicals which are selected, in each case independently of each other, from the group hydroxyl, C$_1$-C$_8$-alkyl, cyano, COOH, COOM, where M is an alkali metal ion or a half equivalent of an alkaline earth metal ion, COO—(C$_1$-C$_4$-alkyl), O—(C$_1$-C$_4$-alkyl), N(C$_1$-C$_4$-alkyl)$_2$, NH—(C$_1$-C$_4$-alkyl), NO$_2$, fluorine, chlorine, bromine, C$_1$-C$_4$-fluoroalkyl, CONH$_2$ and CONH—(C$_1$-C$_4$-alkyl), and R$^2$ and R$^3$ are, in each case independently of each other, hydrogen, C$_1$-C$_8$-alkyl, C$_4$-C$_{14}$-aryl or C$_5$-C$_{15}$-arylalkyl, or the two radicals R$^2$ and R$^3$ are together C$_3$-C$_{12}$-alkylene, comprising:

a) reducing compounds of the formula (I)

heteroaryl-CO—CH$_2$W (I), in which heteroaryl is defined as in formula (IV), and W is C(O)YR$^1{}_n$, where Y is =oxygen and n is =1 or Y is nitrogen and n is =2, or W is CN, and R$^1$ are, in each case independently of each other, hydrogen, C$_1$-C$_8$-alkyl, C$_4$-C$_{10}$-aryl or C$_5$-C$_{11}$-arylalkyl or, when Y is nitrogen, the two radicals R$^1$ are together C$_3$-C$_5$alkylene, by contacting said compounds of the formula (I) with microorganisms selected from the group consisting of *Saccharomyces cerevisiae* NG 247, *Saccharomyces cereviseae* Y278 and *Geotrichum candidum* ATCC 34614; in the presence of water having a pH range of from 3 to 11, based on 25° C.;

to yield enantiomer-enriched compound of formula (II), heteroaryl-CH(OH)—CH$_2$W (II)

where, in each case, heteroaryl and W have the meanings mentioned under formula (I), and b) performing one of the following manipulations, i) when W is CON(R$^1$)$_2$ and the R$^1$ radicals are in each case, independently of each other, hydrogen, C$_1$-C$_8$-alkyl, C$_4$-C$_{10}$-aryl or C$_5$-C$_{11}$-arylalkyl, or the two R$^1$ radicals are together C$_3$-C$_5$-alkylene, reacting the enantiomer-enriched compounds of formula (II) with amines of the formula (III)

HNR$^2$R$^3$ (III)

in which R$^2$ and R$^3$ have the meaning mentioned under formula (VI), to give enantiomer-enriched compounds of the formula (IV), heteroaryl-CH(OH)—CH$_2$—CO—NR$^2$R$^3$ (IV)

in which heteroaryl, R$^2$ and R$^3$ have the previously mentioned meanings, or when W is CN, aminolyizing/hydrolyzing the compounds of the formula (II) directly to yield compounds of the formula (IV), or initially hydrolyzing, partially hydrolyzing or both alcoholyzing/hydrolyzing the compounds of formula (II) to yield compounds of the formula (V)

heteroaryl-CH(OH)—CH$_2$—CO—R$^4$ (V)

in which heteroaryl has the meaning given under formula (I) and R$^4$ is OR$^1$ or NH$_2$, where R$^1$ has the abovementioned meaning, and amidating the compound of formula (V) to yield enantiomer-enriched compounds of the formula (IV), and c) reducing the enantiomer-enriched compounds of the formula (IV) to yield enantiomer-enriched compounds of the formula (VI) having the abovementioned meaning.

2. Process according to claim 1, characterized in that, in the formulae (III), (IV) and (VI), R$^2$ and R$^3$ are, in each case, independently selected from hydrogen, methyl, ethyl, isopropyl, phenyl or benzyl.

3. Process according to claim 1, characterized in that compounds of the formula (I) in which W is not CN are obtained by reacting compounds of the formula (VII)

heteroaryl-CO—CH$_3$ (VII)

in which heteroaryl has the meaning mentioned under formula (I), with compounds of the formula (VIII),

R$^1$—O—W (VIII)

in which

R$^1$ and W have the same meanings as those which were given under the formula (I), with W not being CN, in the presence of a base.

4. Process according to claim 1, characterized in that the reduction of compounds of the formula (VI) is effected using complex boron hydrides or aluminium hydrides.

5. Process according to claim 1, characterized in that (1S)-3-(methylamino)-1-(2-thiophenyl)-1-propanol, (1R)-3-(methylamino)-1-(2-thiophenyl)-1-propanol, (1S)-3-(dimethylamino)-1-(2-thiophenyl)-1-propanol or (1R)-3-(dimethylamino)-1-(2-thiophenyl)-1-propanol is prepared.

6. Process according to claim 1, characterized in that in a further step d), the enantiomer-enriched compounds of the formula (VI) are reacted, in the presence of base, with compounds of the formula (XI)

R$^6$-Hal (XI)

in which

R$^6$ is phenyl or naphthyl which is optionally substituted, once or more than once, by substituents which are selected, in each case independently of each other, from the group cyano, CO—(C$_1$-C$_{12}$-alkyl), O—(C$_1$-C$_{12}$-alkyl), (C$_1$-C$_{12}$-alkyl), fluorine, chlorine, bromine and C$_1$-C$_{12}$-fluoroalkyl, and Hal is fluorine, chlorine, bromine or iodine,
to give enantiomer-enriched compounds of the formula (X),

in which heteroaryl, $R^2$ and $R^3$ have the meaning given under formula (I) and $R^6$ has the meaning given under formula (XI).

7. Process according to claim 6, characterized in that (S)-N-methyl-3-(1-naphthalenyloxy)-3-(2-thienyl)propylamine and (R)-N-methyl-3-(1-naphthalenyloxy)-3-(2-thienyl)propylamine, or their ammonium salts, are prepared.

8. Process according to claim 1, characterized in that W is $C(O)YR^1{}_n$, where Y is =oxygen and n is =1 or Y is nitrogen and n is =2.

9. Process according to claim 1, characterized in that W is CN.

10. Process according to claim 1, which comprises contacting said compounds of the formula (I) with *Saccharomyces cereviseae* NG 247.

11. Process according to claim 1, which comprises contacting said compounds of the formula (I) with *Saccharomyces cerevisiae* Y278.

12. Process according to claim 1, which comprises contacting said compounds of the formula (I) with *Geotrichum candidum* ATCC 34614.

* * * * *